US00PP34433P2

(12) United States Plant Patent
Spil

(10) Patent No.: US PP34,433 P2
(45) Date of Patent: Jul. 19, 2022

(54) ***ECHINACEA* PLANT NAMED 'IFECSSTS'**

(50) Latin Name: *Echinacea hybrida*
Varietal Denomination: 'IFECSSTS'

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 17/563,966

(22) Filed: Dec. 28, 2021

Related U.S. Application Data

(60) Provisional application No. 63/133,902, filed on Jan. 5, 2021.

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Echinacea* plant named 'IFECSSTS', characterized by its upright and relatively compact plant habit; moderately vigorous growth habit; freely branching habit; strong flowering stems; numerous and large single-type inflorescences with orange yellow and red bi-colored ray florets and greyed red-colored receptacle spines; and good garden performance.

2 Drawing Sheets

Figure 1:
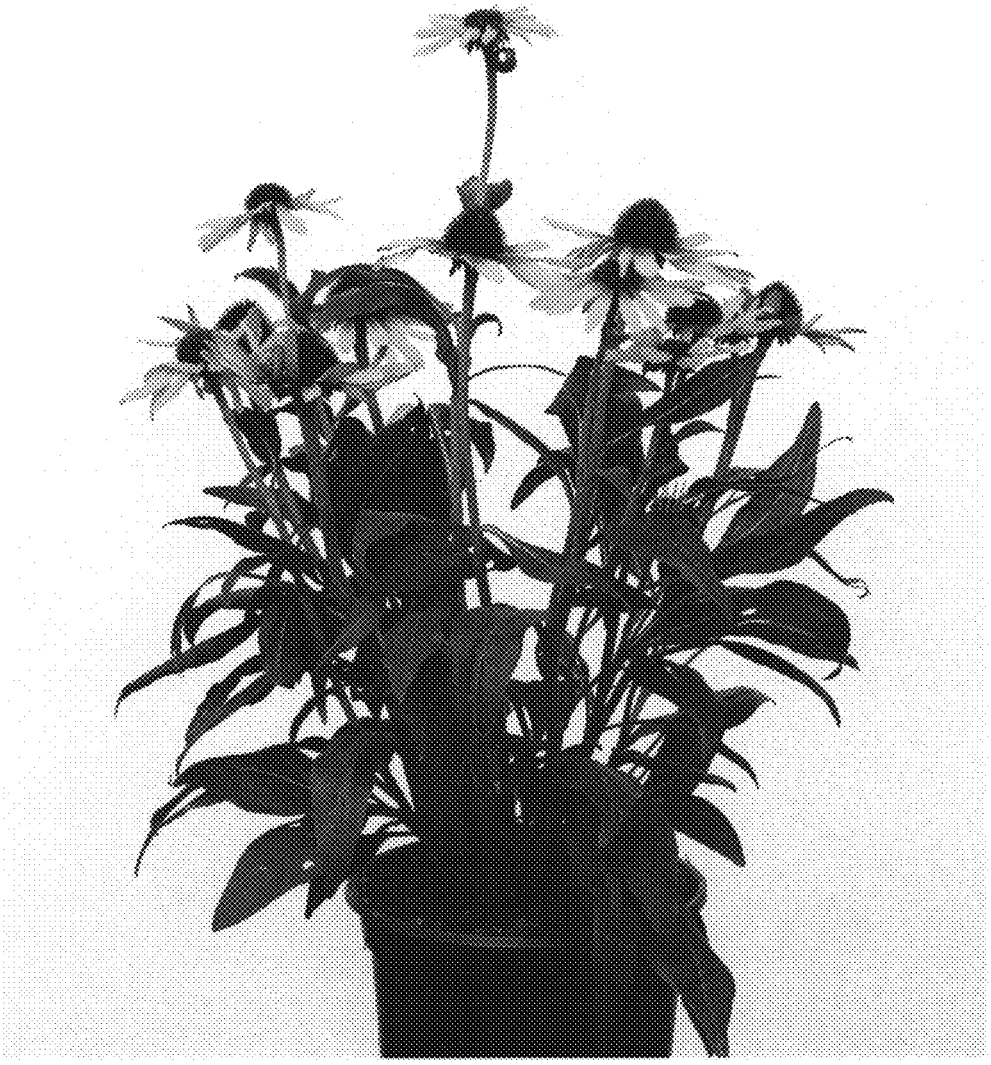

Botanical designation: *Echinacea hybrida.*
Cultivar denomination: 'IFECSSTS'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Innoflora Plant Breeding B.V. of Heerhugowaard, The Netherlands on Nov. 6, 2020, application number 2020/2809. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Echinacea* plant, botanically known as *Echinacea hybrida*, and hereinafter referred to by the name 'IFECSSTS'.

The new *Echinacea* plant is a product of a planned breeding program conducted by the Inventor in Heerhugowaard, The Netherlands. The objective of the breeding program is to develop new vigorous and freely flowering *Echinacea* plants with large inflorescences with unique and attractive ray floret coloration.

The new *Echinacea* plant originated from a cross-pollination in July, 2017 in Heerhugowaard, The Netherlands of a proprietary selection of *Echinacea hybrida* identified as code number 009-15-K054-01, not patented, as the female, or seed, parent with a proprietary selection of *Echinacea hybrida* identified as code number 009-14-K070-032, not patented, as the male, or pollen, parent. The new *Echinacea* plant was discovered and selected by the Inventor as a single flowering plant from within the progeny of the stated cross-pollination grown in a controlled greenhouse environment in Heerhugowaard, The Netherlands in August, 2018.

Asexual reproduction of the new *Echinacea* plant by in vitro meristem culture in a controlled environment in Heerhugowaard, The Netherlands since September, 2019 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'IFECSSTS'. These characteristics in combination distinguish 'IFECSSTS' as a new and distinct *Echinacea* plant:

1. Upright and relatively compact plant habit.
2. Moderately vigorous growth habit.
3. Freely branching habit.
4. Strong flowering stems.

5. Numerous and large single-type inflorescences with orange yellow and red bi-colored ray florets and greyed red-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are more compact than plants of the female parent selection.
2. Plants of the new *Echinacea* and the female parent selection differ in ray floret color as plants of the new *Echinacea* have orange yellow and red bi-colored ray florets whereas plants of the female parent selection have red-colored ray florets.

Plants of the new *Echinacea* can be compared to plants of the male parent selection. Plants of the new *Echinacea* differ primarily from plants of the male parent selection in the following characteristics:

1. Plants of the new *Echinacea* and the male parent selection differ in ray floret color as plants of the new *Echinacea* have orange yellow and red bi-colored ray florets whereas plants of the male parent selection have orange-colored ray florets.
2. Ray florets of plants of the new *Echinacea* are held mostly erect to horizontal whereas ray florets of plants of the male parent selection are drooping.

Plants of the new *Echinacea* can be compared to plants of *Echinacea hybrida* 'Parrot', disclosed in U.S. Plant Pat. No. 31,928. In side-by-side comparisons, plants of the new *Echinacea* differ primarily from plants of 'Parrot' in the following characteristics:

1. Plants of the new *Echinacea* are more compact than plants of 'Parrot'.
2. Plants of the new *Echinacea* are more freely branching than plants of 'Parrot'.
3. Leaves of plants of the new *Echinacea* are smaller and more upright than leaves of plants of 'Parrot'.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet (FIG. 1) is a side perspective view of a typical flowering plant of 'IFECSSTS' grown in a container.

Figure 2:
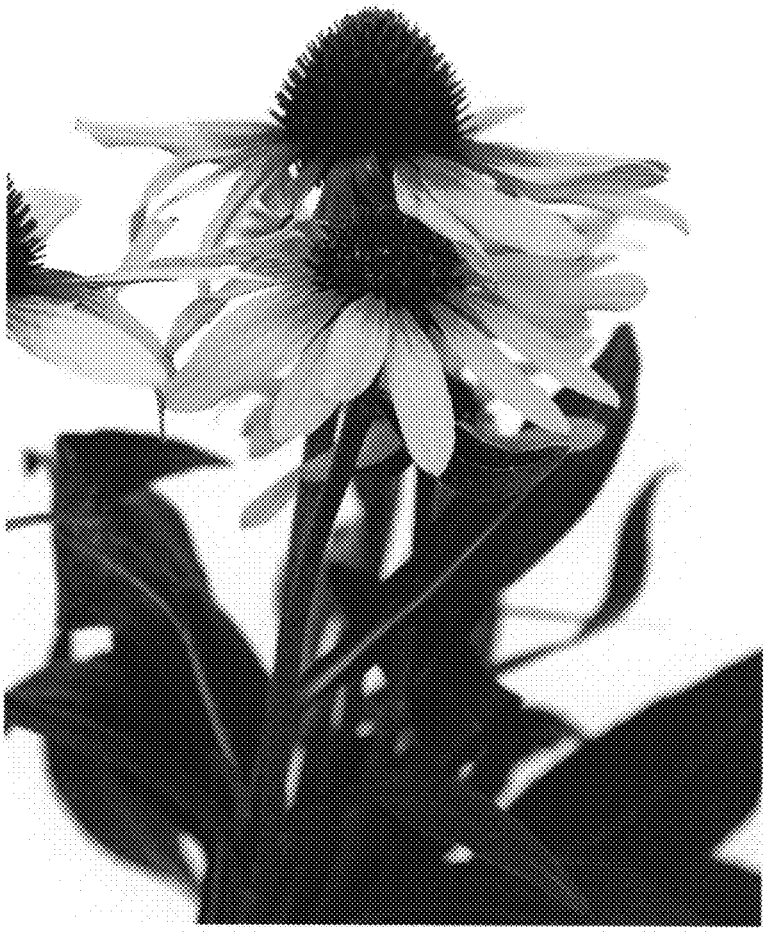

The photograph at the top of the second sheet (FIG. 2) is a close-up view of typical inflorescences of 'IFECSSTS'.

Figure 3:
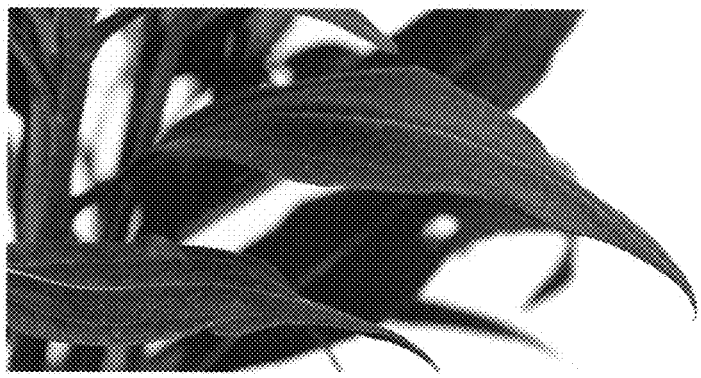

The photograph at the bottom of the second sheet (FIG. 3) is a close-up view of typical leaves of 'IFECSSTS'.

DETAILED BOTANICAL DESCRIPTION

The aforementioned photographs and following observations and measurements describe plants grown during the late summer in 17-cm containers in an outdoor nursery in Heerhugowaard, The Netherlands and under cultural practices typically used in commercial *Echinacea* production. During the production of the plants, day temperatures ranged from 16° C. to 30° C. and night temperatures ranged from 8° C. to 18° C. Plants were pinched eight weeks after planting and were two years old when the photographs and description were taken. In the following description, color references are made to The Royal Horticultural Society Colour Chart, 2015 Edition, except where general terms of ordinary dictionary significance are used.

Botanical classification: *Echinacea hybrida* 'IFECSSTS'.

Parentage:

*Female parent*.—Proprietary selection of *Echinacea hybrida* identified as code number 009-15-K054-01, not patented.

*Male parent*.—Proprietary selection of *Echinacea hybrida* identified as code number 009-14-K070-02, not patented.

Propagation:

Type: By in vitro meristem culture.

*Time to initiate roots, summer*.—About twelve days at temperatures about 20° C.

*Time to initiate roots, winter*.—About 16 days at temperatures about 20° C.

*Time to produce a rooted young plant, summer*.—About 36 days at temperatures about 18° C.

*Time to produce a rooted young plant, winter*.—About 42 days at temperatures about 18° C.

*Root description*.—Thick, fleshy; typically white in color, actual color of the roots is dependent on substrate composition, water quality, fertilizer type and formulation, substrate temperature and physiological age of roots.

*Rooting habit*.—Moderately freely branching; sparse.

Plant description:

*Plant form and growth habit*.—Herbaceous perennial; upright and relatively compact plant habit, inverted triangle; freely basal branching habit with about 16 primary lateral branches developing per plant; moderately vigorous growth habit and moderate growth rate.

*Plant height*.—About 48 cm.

*Plant diameter or spread*.—About 40.8 cm.

*Lateral branches*.—Length: About 23.8 cm. Diameter: About 6 mm. Internode length: About 3.2 cm. Aspect: Erect to about 15° from vertical. Strength: Strong. Texture: Densely pubescent; strigose, rough. Color: Close to 144B.

Leaf description:

*Basal leaves*.—Arrangement: Alternate, simple. Length: About 13.2 cm. Width: About 4.6 cm. Shape: Narrowly ovate. Apex: Acute to narrowly acute. Base: Attenuate. Margin: Entire to coarsely and shallowly dentate; slightly and coarsely undulate. Texture and luster, upper and lower surfaces: Moderately pubescent, strigose and rough; matte. Venation pattern: Pinnate. Color: Developing leaves, upper surface: Close to 137B. Developing leaves, lower surface: Close to between 146A and 146B. Fully expanded leaves, upper surface: Darker than close to NN137A and 147A; venation, close to 144B. Fully expanded leaves, lower surface: Slightly darker 147B; venation, close to 146D.

*Cauline leaves*.—Arrangement: Alternate, simple. Length: About 12.2 cm. Width: About 3.7 cm. Shape: Narrowly ovate. Apex: Acute to narrowly acute. Base: Attenuate. Margin: Entire to coarsely and shallowly dentate; slightly and coarsely undulate. Texture and luster, upper and lower surfaces: Moderately pubescent, strigose and rough; matte. Venation pattern: Pinnate. Color: Developing leaves, upper surface: Close to 137B. Developing leaves, lower surface: Close to between 146A and 146B. Fully expanded leaves, upper surface: Darker than close to NN137A and 147A; venation, close to 144B. Fully expanded leaves, lower surface: Slightly darker than 147B; venation, close to 146D.

*Petioles, basal leaves*.—Length: About 9.2 cm. Diameter: About 2.25 mm by 4 mm. Texture, upper surface: Smooth, glabrous. Texture, lower surface: Mostly glabrous; midvein and margins, sparsely pubescent. Color, upper surface: Close to NN137B; midvein, close to 146D. Color, lower surface: Close to NN137B; midvein, close to 144B.

*Petioles, cauline leaves*.—Length: About 4 cm. Diameter: About 2.25 mm by 4 mm. Texture, upper surface: Smooth, glabrous. Texture, lower surface: Mostly glabrous; midvein and margins, sparsely pubescent. Color, upper surface: Close to NN137B; midvein, close to 146D. Color, lower surface: Close to NN137B; midvein, close to 144B.

Inflorescence description:

*Appearance*.—Large single-type inflorescences with ray and disc florets arranged on a capitulum; inflorescences positioned upright above the foliar plane on mostly upright and strong peduncles.

*Flowering habit*.—Freely flowering habit with about 32 developing and fully developed inflorescences per plant.

Fragrance: Moderately fragrant; sweet and pleasant.

*Time to flower*.—Plants flower continuously from early July to late September in The Netherlands.

*Inflorescence longevity*.—Inflorescences maintain good substance for about three weeks on the plant; inflorescences persistent.

*Inflorescence buds*.—Height: About 2 cm. Diameter: About 2.3 cm. Shape: Flattened globular. Color: Close to 146A.

*Inflorescence size*.—Diameter: About 10.4 cm. Depth (height): About 3.6 cm. Disc diameter: About 3.4 cm.

*Receptacles*.—Height: About 1.1 cm. Diameter: About 1 cm. Shape: Deltoid. Color: Close to 155B.

*Ray florets*.—Quantity and arrangement: About 15 to 21 arranged in a single whorl at the base of the receptacle. Length: About 4.9 cm. Width: About 1.1 cm. Shape: Narrowly oblong to oblanceolate; slightly carinate. Apex: Emarginate. Base: Cuneate. Margin: Entire. Texture and luster, upper surface: Smooth, glabrous; velvety; matte. Texture and luster, lower surface: Smooth, glabrous; slightly glossy. Aspect: Mostly horizontal; with development, reflexing slightly downward with development. Color: When opening, upper surface: Close to 23B and towards the base, close to 42C to 42D. When opening, lower surface: Close to 11B and towards the base, close to 147C with basal margins, close to 54A. Fully opened, upper surface: Distally, close to 21B and proximally, close to 53A to 53B; venation, similar to lamina; color distally becoming closer to 20A and proximally, closer to 60A, with subsequent development. Fully opened, lower surface: Distally, close to 150B and proximally, close to 145A, with margins, close to 59A; venation, close to 145A to 145B; color becoming closer to between 149B and 150A and basal margins, closer to 183C, with subsequent development.

*Disc florets*.—Quantity and arrangement: About 220 per inflorescence, arranged spirally at the center of the inflorescence. Length: About 1 cm. Diameter: About 2 mm. Shape: Tubular; proximally, 17.5% free, not fused. Apex: Acute. Base: Fused. Margin, free-part: Entire. Texture and luster, inner and outer surfaces: Smooth, glabrous; moderately glossy. Color, when opening, inner and outer surfaces: Apex: Close to 176B. Mid-section: Close to 143C. Base: Close to 150C. Color, fully opened, inner and outer surfaces: Apex and mid-section: Close to 148A tinged with close to 183C. Base: Close to 144C.

*Receptacle spines*.—Quantity: One per disc floret; about 220 per inflorescence. Shape: Acicular. Apex: Acute. Base: Attenuate. Texture and luster: Smooth, glabrous; glossy. Color: Apex: Close to 179A. Mid-section: Close to 146C. Base: Close to 145D.

*Involucral bracts*.—Quantity per inflorescence: About 60 arranged in about four whorls. Length: About 1 cm. Width: About 2 mm. Shape: Narrowly ovate; strongly reflexed. Apex: Acute. Base: Cuneate. Margin: Entire. Texture and luster, upper surface: Smooth, glabrous; slightly glossy. Texture, lower surface: Moderately pubescent. Color, upper surface: Close to NN137A. Color, lower surface: Close to 138A.

*Peduncles*.—Length: About 10.3 cm. Diameter: About 4.5 cm. Strength: Strong. Aspect: Mostly upright. Texture: Moderately to densely pubescent; strigose. Color: Close to 144A and 144B.

*Reproductive organs*.—Androecium (present on ray and disc florets): Quantity per floret: Five. Filament length: About 3 mm. Filament color: Close to 157D. Anther length: About 2.5 mm. Anther shape: Lanceolate. Anther color: Close to 200A to slightly darker than 200A. Pollen amount: Scarce. Pollen color: Close to 21A. Gynoecium (present only on disc florets): Quantity per floret: One. Pistil length: About 7 mm. Stigma shape: Decurrent, unequal. Stigma color: Close to N186A. Style length: About 5.5 mm. Style color: Slightly lighter than close to 153D. Ovary color: Close to 145D. Seeds and fruits: To date, seed and fruit development have not been observed on plants of the new *Echinacea*.

Pathogen & pest resistance: To date, plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'IFECSSTS' as illustrated and described.

* * * * *